(12) United States Patent
McCreary et al.

(10) Patent No.: US 8,106,056 B2
(45) Date of Patent: Jan. 31, 2012

(54) COMBINATION PREPARATIONS COMPRISING BIFEPRUNOX AND A DOPAMINE AGONIST

(75) Inventors: Andrew C. McCreary, Weesp (NL); Gustaaf J. M. Van Scharrenburg, Weesp (NL); Martinus Th. M. Tulp, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 958 days.

(21) Appl. No.: 11/762,239

(22) Filed: Jun. 13, 2007

(65) Prior Publication Data
US 2007/0293506 A1   Dec. 20, 2007

Related U.S. Application Data

(60) Provisional application No. 60/814,052, filed on Jun. 16, 2006.

(51) Int. Cl.
*A61K 31/497* (2006.01)
*A61K 31/195* (2006.01)
*A61K 31/16* (2006.01)
*A61K 31/135* (2006.01)

(52) U.S. Cl. .................. 514/254.02; 514/567; 514/564; 514/615; 514/649

(58) Field of Classification Search ........................ None
See application file for complete search history.

(56) References Cited

U.S. PATENT DOCUMENTS

| 6,500,867 B1 * | 12/2002 | Virkki et al. ................. 514/646 |
| 2004/0077631 A1 | 4/2004 | Van Aar et al. |
| 2005/0107396 A1 * | 5/2005 | Eijgendaal et al. ...... 514/254.02 |
| 2005/0234389 A1 | 10/2005 | Bouwstra et al. |

FOREIGN PATENT DOCUMENTS

| EP | 0 908 458 A1 | 4/1999 |
| EP | 0 189 612 A1 | 8/2006 |
| WO | WO 97/36893 | 10/1997 |
| WO | WO 00/29397 | 5/2000 |
| WO | WO 01/74365 | 10/2001 |
| WO | WO 01/85725 | 11/2001 |
| WO | WO 02/066449 | 8/2002 |
| WO | WO 2004089353 A2 * | 10/2004 |
| WO | WO 2006/032202 A1 | 3/2006 |
| WO | WO 2006/061372 | 6/2006 |
| WO | WO 2006/087369 | 8/2006 |
| WO | WO 2007/02341 A1 | 3/2007 |

OTHER PUBLICATIONS

Chawla et al., "Challenges in Polymorphism of Pharmaceuticals," CRIPS, Jan.-Mar. 2004, vol. 5, No. 1, pp. 9-12.*
Newman et al., "Solid-state analysis of the active pharmaceutical ingredient in drug products," DDT, Oct. 2003, vol. 8, No. 9, pp. 898-905.*
"Bifeprunox—Atypical Antipsychotic Drug," Drug Development Technology, pp. 1-3, 2007, www.drugdevelopment-technology.com/projects/bifeprunox/.
"Solvay Announces New Drug Plans for Schizophrenia," Schizophernia Daily New Blog, pp. 1-4 (2004), www.schizophrenia.com/sznews/archives/000573.html.
Berendsen, et al., "Selective Activation of 5HT1A Receptors Induces Lower Lip Retraction in the Rat," Pharmacology Biochemistry & Behavior, vol. 33, pp. 821-827, 1989.
Bickel, M.H., "The Pharmacology and Biochemistry of N-Oxides," Pharmacological Reviews, vol. 21, No. 4, pp. 325-355, 1969.
Costall et al., "Differential actions of typical and atypical neuroleptic agents on two behavioural effects of apomorphine in the mouse," Proceedings of the B.P.S., pp. 381-381, 1978.
Creese et al., "3H-Spiroperidol Labels Dopamine Receptors in Pituitary and Brain," European Journal of Pharmacology, 46, pp. 377-381, 1977.
Fleischhacker, "Clozapine: A Comparison With Other Novel Antipsychotics," J. Clin Psychiatry, vol. 60, No. 12, 1999, pp. 30-34.
Gozlan, et al., "Identification of presynaptic serotonin autoreceptors using a new ligand: 3H-PAT," Nature, vol. 305, pp. 140-142, 1983.
Haleblian et al., "Pharmaceutical Applications of Polymorphism," Journal of Pharmaceuticals Sciences, vol. 58, No. 8, 1969, pp. 911-929.

(Continued)

*Primary Examiner* — Sreeni Padmanabhan
*Assistant Examiner* — Jody Karol
(74) *Attorney, Agent, or Firm* — Finnegan, Henderson, Farabow, Garrett & Dunner LLP (57) ABSTRACT

The present invention relates to a composition containing bifeprunox or its N-oxide, or at least one pharmacologically acceptable salt thereof:

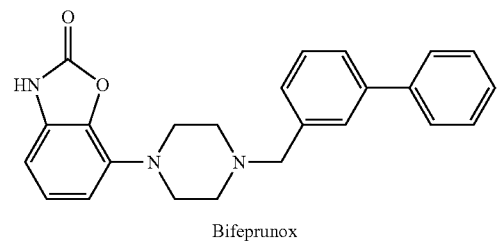

Bifeprunox

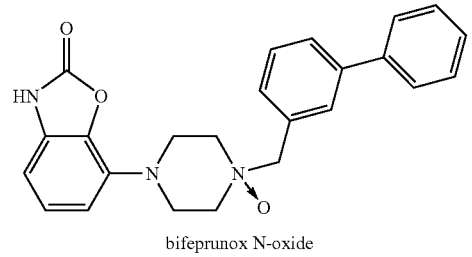

bifeprunox N-oxide and L-DOPA or at least one pharmacologically acceptable salt thereof, for simultaneous, separate or sequential use in the treatment of disorders requiring recovery of dopaminergic function, including Parkinson's disease and restless leg syndrome.

13 Claims, 4 Drawing Sheets

OTHER PUBLICATIONS

Kim, et al., "Risperidone Dosing Pattern and Clinical Outcome in Psychosis: An Analysis of 1713 Cases," J. Clin Psychiatry, vol. 66, No. 7, 2005, pp. 887-893.
Robichaud et al., Annual Reports in Medicinal Chemistry, Recent Advances in Selective Serotonin Receptor Modulation, pp. 11-20 (2000).
Salomon, et al., "A Highly Sensitive Adenylate Cyclase Assay," Analytical Biochemistry, 58, pp. 541-548, 1974.
Sorbera, et al., "Treatment of Bipolar Disorder Treatment of Schizophrenia Dopamine D2 Receptor Partial Agonist 5-HT1A Receptor Agonist," Drugs of the Future, pp. 992-997, 2005, vol. 30, No. 10.
Taniguchi et al., "Clozapine Dosage and Titration," Annals of Pharmacotherapy, vol. 30, No. 7-8, 1996, p. 883.
Weiss et al., "Corticotropin-Peptide Regulation of Intracellular Cyclic AMP Production in Cortical Neurons in Primary Culture," Journal of Nurochemistry, vol. 45, No. 3, pp. 869-874, 1985.
Widmark, "Studies in the concentration of indifferent narcotics in blood and tissues," Acta Medica Scandinavica, 52, pp. 87-164, 1919.
Copending U.S. Appl. No. 10/920,361, filed Aug. 18, 2004.
Copending U.S. Appl. No. 10/920,386, filed Aug. 18, 2004.
Copending U.S. Appl. No. 11/354,652, filed Feb. 16, 2006.
Copending U.S. Appl. No. 11/727,173, filed Mar. 23, 2007.
Copending U.S. Appl. No. 11/743,049, filed May 1, 2007.
Copending U.S. Appl. No. 11/762,206, filed Jun. 13, 2007.
Copending U.S. Appl. No. 11/847,197, filed Aug. 29, 2007.
Copending U.S. Appl. No. 11/847,458, filed Aug. 30, 2007.
Allen, Richard P. et al., "Augmentation of the Restless Legs Syndrome With Carbidopa/Levedopa," American Sleep Disorders Association and Sleep Research Society, Sleep, vol. 19, No. 3, pp. 205-213 (1996).
Allen, Richard P., et al. "A Review of Clinical and Pathophysiologic Features," Journal of Clinical Neurophysiology, vol. 18, No. 2, pp. 128-147 (2001).
Bara-Jimenez et al., "Effects of Serotonin 5-HT1A Agonist in Advanced Parkinson's Disease," Movement Disorders, vol. 20, No. 8, pp. 932-936 (2005).
Bennett, Jr., James P., et al., "Pramipexole—A new dopamine agonist for the treatment of Parkinson's Disease," Journal of Neurological Sciences, vol. 163, pp. 25-31 (1999).
Bibbiani, Francesco et al., "Serotonin 5-HT1A Agonist Improves Motor Complications In Rodent and Primate Parkinsonian Models," Neurology, vol. 57, pp. 1829-1834 (2001).
Blandini, Fabio, et al., "Functional Changes of the Basal Ganglia Circuitry in Parkinson's Disease," Progress in Neurobiology, vol. 62, pp. 63-88 (2000).
Chesson, Jr., Andrew L., et al., "Practice Parameters for the Treatment of Restless Legs Syndrome and Periodic Limb Movement Disorder," Sleep, vol. 22, No. 7, pp. 961-968 (1999).
Christoffersen, Curt L., et al., "Reversal of Haloperiodol-Induced Extrapyramidal Side effects in Cebus Monkeys by 8-Hydroxy-2-(di-n-propylamino)tetralin and its Enantiomers," American College of Neuropsychopharmacology, vol. 18, No. 5, pp. 399-402 (1998).
Earley, Christopher J., et al., "Movements During Sleep" "Pergolide and Carbidopa/Levedopa Treatment of the Restless Legs Syndrome and Periodic Leg Movements in Sleep in a Consecutive Series of Patients," Sleep, vol. 19, No. 10, pp. 801-810 (1996).
Feenstra, Rolf W., et al., "New 1-Aryl-4-(biarylmethylene) piperazines as Potential Atypical antipsychotics Sharing Dopamine $D_2$-Receptor and Serotonin 5-$HT_{1A}$-Receptor Affinities," Bioorganic & Medicinal Chemistry Letters 11, pp. 2345-2349 (2001).
Feenstra, Rolf W., et al., "New Approaches for Psychosis Treatment: Design, Synthesis and SAR of Ligands Binding to Dopamine-$D_2$- and Serotonin 5-$HT_{1A}$ Receptors," Drugs of the Future, vol. 27, Suppl. A, p. 226 (P237), XVIIth International Symposium on Medicinal Chemistry (2002).
Hening, Wayne A. et al., "Dyskinesias While Awake and Periodice Movements in Sleep in Restless Legs Syndrome: Treatment with Opioids," Official Journal of the American Academy of Neurology, vol. 36, pp. 1363-1366 (1986).
Hening, Wayne et al., "The Treatment of Restless Legs Syndrome and Periodic Limb Movement Disorder," Sleep, vol. 22, No. 7, pp. 970-999 (1999).
Hesselink, M.B., et al., "P2151" "DU127090, SLV308 and SLV318: Characterization of a Chemically Related Class of Partial Dopamine Agonists with Varying Degrees of 5-HT1A Agonism," EFNS European Journal of Neurology, vol. 10 (Suppl. 1), pp. 125-204 (2003).
Hornykiewicz, Oleh, "Dopamine (3-Hydroxytyramine) and Brain Function," Pharmaceutical Reviews, vol. 18, No. 2, pp. 925-964 (1966).
Jankovic, Joseph, "Natural Course and Limitations of Levodopa Therapy," Official Journal of the American Academy of Neurology, vol. 43, No. 2, Supplement 1, pp. S1-14 thru S1-17 (1993).
Jenner, Peter, "Pharmacology of Dopamine Agonists in the Treatment of Parkinson's Disease," Neurology vol. 58 (Suppl. 1), pp. S1-S8 (2002).
Johnston, L.C., et al., P2158, "Association between Instrinsic Activity and the Antiparkinsonian Effects of a Novel Dopamine D2 Agonist series in the 1-methyl-4phenyl-1,2,3,6-tetrahydeopyridine Treated Primate Model of Parkinson's Disease," EFNS European Journal of Neurology, vol. 10 (Suppl. 1), pp. 169-170 (2003).
Jost, W.H., et al., "Efficacy and tolerability of Stalevo® in Patients with Parkinson's Disease Experiencing Wearing-off," Akt Neurol, vol. 32, Supplement 6, pp. S318-S325 (2005) (XP009074453).
Kannari, Kazuya et al.., "Tandospirone Citrate, a selective 5-$HT_{1A}$ Agonist, Alleviates L-DOPA-Induced Dyskinesia in Patients with Parkinson's Disease," Brain and Nerve, No to shinkei, vol. 54, No. 2, pp. 133-137 (2002).
Lange, Klause W. et al., "Terguride Stimulates Locomotor Activity at 2 Months but Not 10 Months after 1-methyl-4-phenyl-1,2,3,6-tetrahydropyridine Treatment of Common marmosets," European Journal of Pharmacology, vol. 212, pp. 247-252 (1992).
Langston, J. William et al., "MPTP: Current Concepts and Controversies," Clinical Neuropharmacology, vol. 9, No. 6, pp. 485-507 (1986).
Langston, J. William, et al., "MPTP-induced Parkinsonism in Human and Non-human Primates—Clinical and Experimental Aspects," Acta Neurol Scan, vol. 70 (Suppl. 100), pp. 49-54 (1984).
Lledó, A., "Dopamine agonists: The Treatment for Parkinson's Disease in the XXI Century?," Parkinsonism and Related Disorders, vol. 7, pp. 51-58 (2001).
Lozano, Andreas M., et al., "New Developments in Understanding the Etiology of Parkinson's Disease and in its Treatment," Current Opinion in Neurobiology, vol. 8, pp. 783-790 (1998).
Lundbeck, et al., "Bifeprunox Mesilate," Drugs of the Future, vol. 29, No. 9, pp. 938-939 (2004).
Olanow, C. Warren, et al., "Multicenter, Open-Label, Trial of Sarizotan in Parkinson Disease Patients With Levodopa-Induced Dyskinesias (the SPLENDID Study)," Clin Neuropharmacol, vol. 27, No. 2, pp. 58-62 (2004).
Pearce, Ronald K.B., et al., "De Novo Administration of Ropinirole and Bromocriptine Induces Less Dyskinesia Than L-Dopa in the MPTP-Treated Marmoset," Movement Disorders, vol. 13, No. 2, pp. 234-241 (1998).
Pollmächer, Thomas, et al., "Periodic Leg Movements (PLM): Their Relationship to Sleep Stages," Sleep, vol. 16, No. 6, pp. 572-577 (1993).
Rascol, Olivier et al., "A Five-Year Study of the Incidence of Dyskinesia in Patients With Early Parkinson's disease Who Were Treated With Ropinirole or Levodopa," The New England Journal of Medicine, vol. 342, No. 20, pp. 1484-1491 (2000).
Vliet, B.J. Van, et al., "DU 127090: A Highly Potent, Atypical Dopamine Receptor Ligand—High Potency But Low Efficacy at Dopamine $D_2$ Receptors in Vitro," P.2 Psychotic Disorders Andantipsychotics, European College of Neuropsychopharmacology, vol. 10, No. 3, p. S294 (2000).
McCreary, A.C., et al., "SLV308: A Novel Antiparkinsonian Agent With Antidepressant and Anxiolytic Efficacy," 31st Annual Meeting of the Society for Neuroscience Abstracts, vol. 27, Part 1, p. 531 (2001).
McCreary, A.C., et al., "The in vitro characterization of SLV308: A Novel Dopamine $D_5/D_3$ partial Agonist and 5-$HT_{1A}$ Full Agonist for the Treatment of Parkinson's Disease," Movement Disorders, vol. 21, Suppl. 13, pp. S79-S80.
(XP008033520) Wolf, William A., "SLV-308 Solvay," Current Opinion in Investigational Drugs, vol. 4, No. 7, pp. 878-882 (2003).

(XP-002412435) Hesselink, M. et al., "PREV200100499786 abstract," © BIOSIS/BIOSIS, 31$^{st}$ Annual Meeting of the Society for Neuroscience (2001).

(XP-001061442) Johnston, L.C. et al., "134P: The Novel Dopamine D2 Receptor Partial Agonist, SLV-308, Reverses Motor Disability in MPTO-Lesioned Common Marmosets (*CALLITHRIZJACCHUS*)," British Journal of Pharmacology, vol. 133, No. 2 (2001).

(XP-001061489) Feenstra, R. et al., "Antiparkinsonian Antidepressant Anxiolytic Dopamine $D_2$ Partial Agonist 5-$HT_{1A}$ Agonist," Drugs of the Future, vol., 26, No. 2, pp. 128-132 (2001).

(XP-002412436) Johnston, L.C. et al., "PREV200100499785 abstract," © BIOSIS/BIOSIS, 31$^{st}$ Annual Meeting of the Society for Neuroscience (2001).

(XP-001197381) McCREARY, A.C., et al., "SLV308: A Novel Antiparkinsonian Agent With Antidepressant and Anxiolytic Efficacy," Abstracts of the Society for Neuroscience (2001).

(XP-002412438) WPI/Thomson, "AN-2006-253555".

PCT/EP2007/055955, filed Jun. 15, 2007 "European International Search Report and Written Opinion," mailed Sep. 10, 2007.

Office Action (final) issued Feb. 24, 2010, in U.S. Appl. No. 11/762,206.

Office Action dated Aug. 18, 2009, in U.S. Appl. No. 11/762,206.

PCT International Search Report mailed Mar. 31, 2009, in PCT/EP2009/050336.

Salvati, et al., NW-1048 is a novel, reversible and selective MAO-B inhibitor with neuroprotective effects in a model of Parkinson's disease., Society for Neuroscience Abstract, 2000 vol. 26, No. 1-2, pp. abstract No. 765.11.

* cited by examiner

Figure 1 The effect of DU127090 (4mg/kg po) alone or in combination - DOPA (7.5mg/kg po) on locomotor activity in MPTP-treated common marmosets.

FIG. 1

Figure 2 The effect of DU127090 (8mg/kg po) alone or in combination - DOPA (7.5mg/kg po) on locomotor activity in MPTP-treated common marmosets.

FIG. 2

Figure 3 The effect of DU127090 (4 a activity over 7 hours in MPTP-treated common marmosets. * p<0.05 compared to Vehicle-Vehicle (Mann Whitney).

FIG. 3

Figure 4 The effect of DU127090 (4 or 8 mg/kg po) alone or in combination with L-DOPA (7.5mg/kg po) on locomotor 'ON-Time' over 7 hours in MPTP-treated common marmosets. * p<0.05 compared to Vehicle-Vehicle (Mann Whitney).

FIG. 4

Figure 5 The effect of DU127090 (4mg/kg po) alone or in combination with L-DOPA (7.5mg/kg po) on disability score in MPTP-treated common marmosets.

FIG. 5

Figure 6 The effect of DU127090 (8 mg/kg po) alone or in combination with L-DOOPA (7.5mg/kg po) on disability score in MPTP-treated common marmosets.

FIG. 6

Figure 7 The effect of DU127090 (4 or 8 mg/kg po) alone or in combination with L-DOPA (7.5mg/kg po) on total disability scores over 7 hours in MPTP-treated common marmosets. * p<0.05 compared to Vehicle-Vehicle (Mann Whitney).

FIG. 7

Figure 8 The effect of DU127090 (4 or 8 mg/kg po) alone or in combination with L-DOPA (7.5mg/kg po) on disability 'ON-Time' over 7 hours in MPTP-treated common marmosets. * p<0.05 compared to Vehicle-Vehicle (Mann Whitney).

FIG. 8

COMBINATION PREPARATIONS COMPRISING BIFEPRUNOX AND A DOPAMINE AGONIST

This application claims the benefit of priority of U.S. Provisional Application No. 60/814,052, filed on Jun. 16, 2006, the disclosure of which is incorporated by reference herein.

Constant tremors in hands and legs, body movements that gradually become stiffer, slower and weaker, and mask-like facial expressions, are symptoms that have been observed throughout the history of mankind. In 1817 James Parkinson described this cluster of symptoms as 'paralysis agitans', and shortly thereafter the disease was named after the physician who first described it in detail. The pathological cause of Parkinson's disease involves destruction of nerve cells in the substantia nigra, the part of the brain involved with muscle movements. Loss of around 80% of striatal dopamine in Parkinson's disease results in cardinal symptoms of akinesia, rigidity and bradykinesia (Hornykiewicz, O., *Dopamine (3-hydroxytyramine) and brain function*, Pharmacol Reviews, 18, 925-964 (1966)). These patients have problems initiating movement and exhibit postural instability and loss of coordination.

Current Parkinson's disease pharmacotherapy is based on recovery of dopaminergic function (Blandini et al., '*Functional changes of the basal ganglia circuitry in Parkinson's disease*', Prog Neurobiol 62, 63-88 (2000); Lledó, A., '*Dopamine agonists: the treatment for Parkinson's disease in the XXI century?*, Parkinsonism Relat Disord. 7, 51-58 (2000)). Dopamine does not cross the blood brain barrier and cannot therefore be used to treat Parkinson's disease. Its immediate precursor, L-DOPA (the levorotatory enantiomer of 3,4-dihydroxyphenylalanine, also referred to as levodopa) is used instead, because it penetrates the brain where it is decarboxylated to dopamine. However, levodopa is decarboxylated in peripheral tissues too. Thus only a small portion of administered levodopa is transported to the brain. Carbidopa inhibits decarboxylation of peripheral levodopa, but cannot itself cross the blood brain barrier, and has no effect on the metabolism of levodopa in the brain. The combination of carbidopa and levodopa is considered to be the most effective treatment for symptoms of Parkinson's disease. Nevertheless, certain limitations become apparent within two to five years of initiating therapy. As the disease progresses, the benefit from each dose becomes shorter ("the wearing off effect") and some patients fluctuate unpredictably between mobility and immobility ("the on-off effect"), "On" periods are usually associated with high plasma levodopa concentrations and often include abnormal involuntary movements, i.e., dyskinesias. "Off" periods have been correlated with low plasma levodopa and bradykinetic episodes (Jankovic, J., '*Natural course and limitations of levodopa therapy*', Neurology 43: S14-S17 (1993); Rascol et al., *A five-year study of the incidence of dyskinesia in patients with early Parkinson's disease who were treated with ropinirole or levodopa*, N Engl J Med 342: 1484-1491 (2000)). This has prompted clinicians to delay the initiation of L-DOPA treatment by prior treatment with dopaminergic agonists.

However, the use of full dopamine receptor agonists such as apomorphine, bromocryptine, lisuride, pergolide, pramipexol or ropinirole, also has its limitations. They prime for dyskinesias, induce psychotic-like symptoms including hallucinations, orthostatic hypotension, somnolence, and other side-effects (Lozano et al., *New developments in understanding the etiology of Parkinson's disease and in its treatment*, Curr Opin Neurobiol 8: 783-90 (1998); Bennett and Piercey, *Pramipexole—a new dopamine agonist for the treatment of Parkinson's disease*, J Neurol Sci 163: 25-31 (1999)). It has been suggested that this could be overcome by using partial dopamine $D_{2/3}$ receptor agonists, i.e., compounds that do not maximally stimulate dopamine $D_{2/3}$ receptors, (Jenner, P., *Pharmacology of dopamine agonists in the treatment of Parkinson's disease*, Neurology 26: S1-8 (2002)). Such compounds would hypothetically be capable of stimulating dopamine $D_{2/3}$ receptors when the dopaminergic tone is low, while being able to counteract excessive stimulation of the dopamine $D_2$ receptor when the dopaminergic tone is high, thereby resulting in "stabilisation" of dopaminergic transmission in the brain (Jenner, P., *Pharmacology of dopamine agonists in the treatment of Parkinson's disease*, Neurology 26: S1-8 (2002))

$5\text{-HT}_{1A}$ receptor agonists may ameliorate the induction of dyskinesia since the $5\text{-HT}_{1A}$ receptor agonist tandospirone reduced dyskinesia in L-DOPA treated Parkinson's disease patients (Kannari et al., *Tandospirone citrate, a selective $5\text{-HT}_{1A}$ agonist, alleviates L-DOPA induced dyskinesia in patients with Parkinson's disease*, No To Shinkei 54: 133-137 (2002)) and haloperidol-induced extrapyramidal side effects in primates (Christoffersen and Meltzer, *Reversal of haloperidol-induced extrapyramidal side effects in cebus monkeys by 8-hydroxy-2-(di-n-propylamino)tetralin and its enantiomers*, Neuropsychopharmacology 18; 399-402) (1998)). More recently it has been suggested that sarizotan, a $5\text{-HT}_{1A}$ receptor agonist and dopamine receptor ligand, could ameliorate dyskinetic symptoms (Olanow et al., *Multicenter, open label, trial of sarizotan in Parkinson disease patients with levodopa-indiced dyskinesias (the SPLENDID Study)*, Clin Neuropharmacol 27: 58-62 (2004); Bara-Jimenez W et al., *Effects of serotonin $5\text{-HT}_{1A}$ agonist in advanced Parkinson's disease*, Movement Disorders 20: 932-936 (2005); Bibbiani et al., Serotonin $5\text{-HT}_{1A}$ agonist improves motor complications in rodent and primate parkinsonian models, Neurology 57: 1829-1834 (2001)). The presence of $5\text{-HT}_{1A}$ receptor agonist could be beneficial to the therapeutic effects of a partial $D_{2/3}$ receptor agonist (Johnston, L. C., et al., *Association between Intrinsic Activity and the Antiparkinsonian Effects of a Novel Dopamine $D_2$ Agonist series in the 1-methyl-4-phenyl-1,2,3,6-terahydropyridine Treated Primate Model of Parkinson's Disease*, Eur. J. Neurol. 10: S1, 2158 (2003)).

Recently, different combination preparations containing L-DOPA and one or more other enzyme inhibitors have been introduced. Well known are the combinations L-DOPA/carbidopa (e.g., Sinemet®), L-DOPA/benserazide (e.g., Madopar®) and L-DOPA/carbidopa/entacapone (e.g., Stalevo®, (Jost, W. H. et al., '*Efficacy and tolerability of Stalevo® in patients with Parkinson's disease experiencing wearing-off*', Aktuelie Neurologie, 32, Suppl. 6, S318-S325 (2005)). More recently, catecholamine-O-methyltransferase (COMT) inhibitors such as tolcapone and entacapone have been proposed as adjunctive therapy to L-DOPA. These compounds extend the plasma half-life of L-DOPA, without significantly increasing $C_{max}$. Thus, they decrease the duration of wearing-off, but tend to increase the intensity of peak-dose side effects including peak dose dyskinesias. Tolcapone appears to induce significant liver toxicity in a small percentage of patients. Another strategy aimed at slowing down the metabolism of dopamine is the use of monoamine oxidase-B (MAO-B) inhibitors in combination with L-DOPA. The administration of MAO inhibitors, however, is associated with a number of debilitating side effects that limit their use. These effects include, for example, nausea, dizziness, lightheadedness, fainting, abdominal pain, confusion, hallucinations, dry mouth, vivid dreams, dyskinesias, and headache.

Characteristic for combination preparations is that they exist in many different dose combinations, because during the course of the disease usually higher doses of L-DOPA are necessary to keep the symptoms under control. Combination preparations in the form of tablets containing fixed amounts of drugs are easy to use, but simultaneously also offer limited flexibility. An illustration of the fact that fixed combinations are not universally useful is e.g., the use of the selective MAO-B inhibitor selegiline in the treatment of Parkinson's disease. In the early stage of the disease, selegiline may be given as monotherapy: the compound will slow down the metabolism of endogenous dopamine enough to keep the symptoms within tolerable limits. In later stages of the disease, the use of L-DOPA can become necessary. When the efficacy of L-DOPA starts to wear off, usually the first solution to that problem is the use of a decarboxylase inhibitor like carbidopa (see above), and when also that gets insufficient, co-therapy with selegiline will restore L-DOPA's efficacy by reducing the breakdown of the dopamine generated from the L-DOPA. Thus, in practice L-DOPA and selegiline are administered in separate preparations which may be given simultaneously or sequentially.

Victims seriously afflicted with Restless Leg Syndrome (RLS; also known as Ekbom's syndrome), are virtually unable to remain seated or even to stand still. Activities that require maintaining motor rest and limited cognitive stimulation, such as transportation (car, plane, train, etc.) or attending longer meetings, lectures, movies or other performances, become difficult, if not impossible. Tortured by these sensations which become more severe at night, RLS patients find sleep to be virtually impossible, adding to the diminishing quality of their lives. The urge to move, which increases over periods of rest, can be completely dissipated by movement, such as walking. However, once movement ceases, symptoms return with increased intensity. If an RLS patient is forced to lie still, symptoms will continue to build like a loaded spring and, eventually, the legs will involuntarily move, relieving symptoms immediately. Rhythmic or semi-rhythmic movements of the legs are observed if the patient attempts to remain laying down (Pollmacher and Schulz, "*Periodic leg movements (PLM): their relationship to sleep stages*, Sleep 16: 572-577 (1993)). These movements are referred to as dyskinesias-while-awake (DWA) (Hening et al., *Dyskinesias while awake and periodic movements in sleep in restless leg syndrome: treatment with opioids*, Neurology 36: 1363-6 (1986)) or more commonly, periodic limb movements while awake (PLMW). Clinically, RLS is indicated when four diagnostic criteria are met: (1) a sensation of an urge to move the limbs (usually the legs); (2) motor restlessness to reduce sensations; (3) when at rest, symptoms return or worsen; and (4) marked circadian variation in occurrence or severity of RLS symptoms; that is, symptoms worsen in the evening and at night (Allen and Earley, *Restless leg syndrome: a review of clinical and pathophysiologic features*, J Clin Neurophysiol 18: 128-147 (2001)).

Current treatments for RLS are varied and plagued with undesirable side effects. Therapies have included the administration of dopamine agonists, other dopaminergic agents, benzodiazepines, opiates and anti-convulsants. In cases where RLS results from a secondary condition, such as pregnancy, end-stage renal disease, erythropoietin treatment, or iron deficiency, removing the condition, such as by giving birth or treating with traditional iron supplementation, can reduce or eliminate symptoms in at least some cases (Allen, 2001). However, RLS resulting from non-secondary conditions ("idiopathic" RLS), presents a greater treatment challenge. Dopaminergic agents such as levodopa generally provide effective initial treatment, but with continued use, tolerance and symptom augmentation occur in about 80% of RLS patients (Allen and Earley '*Augmentation of the restless leg syndrome with carbidopa/levodopa*, Sleep 19: 205-213 (1996)); this complication is also common for dopamine agonists (Earley and Allen, *Pergolide and carbidopa/levodopa treatment of the restless leg syndrome and periodic leg movements in sleep in a consecutive series of patients*, Sleep 19: 801-810 (1996)). The other alternatives, benzodiazepines, opiates and anti-convulsants are not as uniformly effective as the dopaminergic agents (Chesson et al., *Practice parameters for the treatment of restless leg syndrome and periodic limb movement disorder. An American Academy of Sleep Medicine Report. Standards of Practice Committee of the American Academy of Sleep Medicine*, Sleep 22: 961-968 (1999); Hening et al., *The treatment of restless leg syndrome and periodic limb movement disorder, An American Academy of Sleep Medicine Review*, Sleep 22: 970-999 (1999)). Despite changes in their treatment regimes, 15-20% of patients find that all medications are inadequate because of adverse effects and limited treatment benefit One goal of the present invention was to develop a treatment as effective as L-DOPA, but without its side effects; in particular without its characteristic "on-off effect," causing dyskinesias during "on"-periods, and bradykinetic episodes during "off"-periods.

Surprisingly, in studies in MPTP-treated marmosets, an animal model with predictive value for Parkinson's disease, it was found that combined treatment with L-DOPA and bifeprunox or its N-oxide reduced peak locomotor activity as observed after L-DOPA alone, such that hyperactivity was not observed. The duration of activity ("on"-time) following L-DOPA was increased by co-administration of bifeprunox.

Bifeprunox bifeprunox N-oxide

DU 127090, 7-[4-([1,1'-biphenyl]-3-ylmethyl)-1-piperazinyl]-2(3H)-benzoxazolone, now know as bifeprunox, binds to dopamine $D_2$-like receptors and 5-$HT_{1A}$ receptors; it is a partial agonist at dopamine $D_{2/3}$ receptors and also a partial agonist at serotonin 5-$HT_{1A}$ receptors (WO 97/36893; Van Vliet et al., "*DU 127090; a highly potent, atypical dopamine receptor ligand*". Journal of the European College of Neuropsychopharmacology (ECNP), 10(3), S294 (2000); Feenstra et al., "New 1-aryl-4-(*Biarylmethylene)piperazines as potential atypical anti-psychotic agents with mixed dopamine $D_2$-receptor-and serotonin 5-$HT_{1A}$ receptor affinities*", Bioorg. Med. Chem. Lett., 11, 2345-2349 (2001); Feenstra et al., "New approaches in antipsychotics: design and synthesis of ligands binding to dopamine-$D_2$ and serotonin 5-$HT_{1A}$ receptors, clinical candidates DU 127090 and SLV313"; *Drugs of the Future*, 27 (Suppl. A) (2002); Hesselink et al., *DU 127090, SLV308 and SLV318; characterization of a chemically related class of partial dopamine agonists with varying degrees of 5-$HT_{1A}$ agonism*, Eur. J. Neurol. 10: S1, 2151 (2003); Hesselink et al., *DU 127090, SLV308 and SLV318: characterization of a chemically related class of partial dopamine agonists with varying degrees of 5-$HT_{1A}$ agonism*, Eur. J. Neurol. 10; S1, 2151 (2003); Mealy, N. E., et al., 'Bifeprunox mesylate', Drugs of the Future, 29(9), 938 (2004)). In WO 2007/023141 it was disclosed that in vivo the N-oxide of bifeprunox is rapidly converted to the parent compound, thus functioning as 'prodrug'.

The present invention relates to a composition comprising bifeprunox or its N-oxide, or at least one pharmacologically acceptable salt, hydrate or solvate thereof, and L-DOPA or at least one pharmacologically acceptable salt thereof and, optionally, a decarboxylase inhibitor and/or, optionally, a COMT-inhibitor, and/or, optionally, an MAO-B inhibitor, for simultaneous, separate or sequential use in therapy of disorders requiring recovery of dopaminergic function, in particular Parkinson's disease and 'Restless Leg syndrome'.

The invention relates to the use of bifeprunox or its N-oxide, a true 'prodrug', in cases in which a L-DOPA induces dyskinesias, or can be anticipated to induce dyskinesias. In such cases, the specific pharmacological activities of the compound, viz., partial agonism on dopamine-$D_2$ and dopamine-$D_3$ receptors, as well as full agonism on serotonin 5-$HT_{1A}$ receptors, result in a blockade of the dyskinesias without reducing the therapeutic effect of L-DOPA.

One embodiment of the present invention relates to pharmaceutical formulations, comprising:

(i) bifeprunox, its N-oxide, or at least one pharmacologically acceptable salt, hydrate or solvate thereof, and:
(ii) L-DOPA or at least one pharmacologically acceptable salt thereof, in admixture with a pharmaceutically acceptable adjuvant, diluent or carrier.

Another embodiment of the present invention relates to kits of parts comprising:
(i) a vessel containing bifeprunox, its N-oxide, or at least one pharmacologically acceptable salt, hydrate, or solvate thereof, optionally in admixture with a pharmaceutically acceptable adjuvant, diluent or carrier, and:
(ii) a vessel containing L-DOPA or at least one pharmacologically acceptable salt thereof, optionally in admixture with a pharmaceutically acceptable adjuvant, diluent or carrier, and:
(iii) instructions for the sequential, separate or simultaneous administration of bifeprunox and the L-DOPA, to a patient in need thereof.

Another embodiment of the invention relates to a method of making a kit of parts as defined herein, which method comprises bringing a component (i), as defined above, into association with a component (ii), as defined above, thus rendering the two components suitable for administration in conjunction with each other. Bringing the two components into association with each other, includes that components (i) and (ii) may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Yet another embodiment of the invention relates to methods for treatment of a patient suffering from, or susceptible to, a condition in which recovery of dopaminergic function is required or desired, which method comprises administering to the patient a therapeutically effective total amount of:
(i) bifeprunox, its N-oxide, or at least one pharmacologically acceptable salt, hydrate or solvate thereof, optionally in admixture with a pharmaceutically acceptable adjuvant, diluent or carrier; in conjunction with:
(ii) L-DOPA or at least one pharmacologically acceptable salt thereof, optionally in admixture with at least one pharmaceutically acceptable adjuvant, diluent or carrier.

Still another embodiment of the invention relates to the use of a pharmaceutical formulation, comprising:
(i) bifeprunox, its N-oxide, or at least one pharmacologically acceptable salt, hydrate or solvate thereof, and:
(ii) L-DOPA or at least one pharmacologically acceptable salt thereof, in admixture with at least one pharmaceutically acceptable adjuvant, diluent or carrier, in the manufacture of a medicament for the treatment of a condition in which recovery of dopaminergic function is required or desired.

Definitions

Examples of decarboxylase inhibitors are: carbidopa and benserazide. Examples of catechol-amine-O-methyl transferase (COMT) inhibitors are: entacapone, nitecapone and tolcapone, and monoamine oxidase-B (MAO-B) inhibitors include: deprenyl, (−)-deprenyl (selegiline), desmethyldeprenyl, N-propargyl-1-(R)-aminoindan (rasagaline), phenelzine (nardil), tranyl-cypromine (parnate), CGP3466, furazolidone, isocarboxazid, pargyline, methyclothiazide and procarbazine.

To provide a more concise description, some of the quantitative expressions given herein are not qualified with the term "about". It is understood that whether the term "about"

is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Throughout the description and the claims of this specification the word "comprise" and variations of the word, such as "comprising" and "comprises" is not intended to exclude other additives, components, integers or steps.

The term "composition" as used herein encompasses a product comprising specified ingredients in predetermined amounts or proportions, as well as any product that results, directly or indirectly, from combining specified ingredients in specified amounts. In relation to pharmaceutical compositions, this term encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients. In general, pharmaceutical compositions are prepared by uniformly and intimately bringing the active ingredient into association with a liquid carrier or a finely divided solid carrier or both, and then, if necessary, shaping the product into the desired formulation. The pharmaceutical composition includes enough of the active object compound to produce the desired effect upon the progress or condition of diseases. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

Within the context of this application, the term 'combination preparation' comprises both true combinations, meaning bifeprunox and other medicaments physically combined in one preparation such as a tablet or injection fluid, as well as 'kit-of-parts', comprising bifeprunox and L-DOPA in separate dosage forms, together with instructions for use, optionally with further means for facilitating compliance with the administration of the component compounds, e.g., label or drawings. With true combinations, the pharmacotherapy by definition is simultaneous. The contents of 'kit-of-parts', can be administered either simultaneously or at different time intervals. Therapy being either concomitant or sequential will be dependent on the characteristics of the other medicaments used, characteristics like onset and duration of action, plasma levels, clearance, etc., as well as on the disease, its stage, and characteristics of the individual patient.

The dose of the composition to be administered will depend on the relevant indication, the age, weight and sex of the patient and may be determined by a physician. In one embodiment, the dosage is in a range of from 0.01 mg/kg to 10 mg/kg. The typical daily dose of the active ingredients varies within a broad range and will depend on various factors such as the relevant indication, the route of administration, the age, weight and sex of the patient and may be determined by a physician. In some embodiments, oral and parenteral dosages may be in the range of 0.1 to 1,000 mg per day of total active ingredients.

The term "therapeutically effective amount" as used herein refers to an amount of a therapeutic agent to treat a condition treatable by administrating a composition of the invention. That amount is the amount sufficient to exhibit a detectable therapeutic or ameliorative response in a tissue system, animal or human. The effect may include, for example, treating the conditions listed herein. The precise effective amount for a subject will depend upon the subject's size and health, the nature and extent of the condition being treated, recommendations of the treating physician (researcher, veterinarian, medical doctor or other clinician), and the therapeutics, or combination of therapeutics, selected for administration. Thus, it is not useful to specify an exact effective amount in advance.

The term "pharmaceutically acceptable salt" refers to those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. They can be prepared in situ when finally isolating and purifying the compounds of the invention, or separately by reacting them with pharmaceutically acceptable non-toxic bases or acids, including inorganic or organic bases and inorganic or organic acids. Pharmaceutically acceptable salts may be obtained using standard procedures well known in the art, for example by mixing a compound of the present invention with a suitable acid, for instance an inorganic acid or an organic acid.

"Administration in conjunction with", includes that respective formulations comprising bifeprunox and L-DOPA are administered, sequentially, separately and/or simultaneously, over the course of treatment of the relevant condition, which condition may be acute or chronic. In some embodiments, the two formulations are administered (optionally repeatedly) sufficiently closely in time for there to be a beneficial effect for the patient, that is greater, over the course of the treatment of the relevant condition, than if either of the two formulations are administered (optionally repeatedly) alone, in the absence of the other formulation, over the same course of treatment. Determination of whether a combination provides a greater beneficial effect in respect off and over the course of treatment of, a particular condition, will depend upon the condition to be treated or prevented, but may be achieved routinely by the person skilled in the art. Thus, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses of bifeprunox and L-DOPA are administered within 48 hours, e.g., 24 hours, 18 hours, 12 hours, 6 hours, 3 hours, 2 hours, 1 hour, or 30 minutes of each other.

The term "treatment" as used herein refers to any treatment of a mammalian, such as a human condition or disease, and includes: (1) inhibiting the disease or condition, i.e., arresting its development, (2) relieving the disease or condition, i.e., causing the condition to regress, or (3) stopping the symptoms of the disease.

As used herein, the term "medical therapy" intendeds to include prophylactic, diagnostic and therapeutic regimens carried out in vivo or ex vivo on humans or other mammals.

The term "subject" as used herein, refers to an animal, for example, a mammal, such as a human, who has been the object of treatment, observation or experiment.

EXAMPLES

Treatment with the neurotoxin MPTP (1-methyl-4-phenyl-1,2,3,6-tetrahydropyridine) leads to depletion of dopamine in the caudate-putamen and 'parkinsonian-like' behavior in non-human and human primates (Lange K. W., et al., *Terguride stimulates locomotor activity at 2 months but not 10 months after MPTP-treatment of common marmosets*. Eur J of Pharmacology, 212, 247-52 (1992); Langston et al., *MPTP-induced parkinsonism in humans and non-human primates-Clinical and experimental aspects*, Acta Neurol Scand 70, 49-54 (1984); Langston and Irwin, *MPTP: Current concepts and controversies*. Clin Neuropharmacol 9, 485-507 (1986)).

Example 1

Interaction Between Bifeprunox and L-DOPA

Animals: The study employed common marmosets (*Callithrix jacchus*) (n=6, aged between 3 to 5 years; 5 female and 1 male) previously treated with MPTP (2 mg/kg sc daily) for 5 days and which exhibited stable motor deficits. These animals were L-DOPA responsive and not test drug naive. They had not been experimentally primed for dyskinesia although some dyskinesia was present.

Drug treatment: Bifeprunox mesylate was suspended in 10% sucrose solution and administered orally by gavage in a volume of 2.0 ml/kg. L-DOPA: L-3,4-Dihydroxyphenylalanine (L-dopa) methylester (Sigma Chemical Co, UK) was dissolved in 10% sucrose solution and administered orally by gavage in a volume of 2.0 ml/kg. Carbidopa: (Merck, Sharp and Dohme, UK) was administered orally as a suspension in 10% sucrose solution in a volume of 2.0 ml/kg. Domperidone: (2.0 mg/kg po, Sigma UK) was dissolved in 10% sucrose and administered 60 min prior to bifeprunox in a volume of 2.0 ml/kg, Bifeprunox (4 or 8 mg/kg po free base) or its vehicle (10% sucrose) was administered alone and in combination with L-DOPA (7.5 mg/kg po free base, given in combination with carbidopa, 12.5 mg/kg po) to MPTP-treated marmosets (n=6). Animals were treated with bifeprunox or its vehicle 90 min prior to administration of L-DOPA or its vehicle administration. Carbidopa was administered 30 minutes prior to administration of L-DOPA. Domperidone was administered 60 min prior to bifeprunox administration.

Behavioral Studies: In all studies, animals were acclimatised to behavioral study cages for 1 hour prior to treatment. The animals were placed individually into activity cages (50× 60×70 cm) fitted with a clear perspex door to allow clear visibility for observation. Each cage was equipped with 8 horizontally orientated infrared photocell emitters and their corresponding detectors arranged so as to permit maximum assessment of movement. Locomotor activity was assessed as the number of light beam interruptions caused by movement of the animals accumulated in 10-minute intervals for up to 7 hours. The animals were allowed a 60-minute acclimatisation period in the activity cages during which baseline activity was assessed, before drug administration. 'On' Threshold was defined as 3 times baseline activity in MPTP-treated marmosets. Hyperactivity was defined as 3 times normal activity in naive marmosets. 'On' time was the period of time in minutes that activity was above the 'On' Threshold. Animals were treated with bifeprunox, vehicle and/or L-DOPA. Following drug treatment, animals were assessed for locomotor activity and disability as described below for up to 6 h following drug administration. The animals used in the study were in the automated activity cages for no longer than 8 h on any study day, and were allowed at least 3 days recovery period between drug treatments to ensure appropriate animal welfare consideration. The locomotor activity, motor disability and presence of dyskinesia were assessed as follows:

Locomotor Activity: In all studies the animals were acclimatised to behavioral study cages for 1 hour prior to bifeprunox treatment. Animals were then treated with appropriate drugs. Following treatment, animals were assessed for anti-parkinsonian activity for up to 6 h using automated activity cages and by the rating of disability by an observer blinded to the treatment. Locomotor 'On-time' was defined as the period of time the animals showed activity above 3× baseline locomotor activity or a locomotor activity of 100 which ever was greater.

Disability and dyskinesia scores: Disability and dyskinesia was assessed before, and during the last 10 minutes in every 30 min period after bifeprunox administration for up to 6 hours following drug treatment. The following disability rating scales were used:

Rating of disability: The disability of animals was scored as follows; alertness (normal 0, sleepy 2); reaction (normal 0, reduced 1, slow 2, absent 3); checking movements (present 0, reduced 1, absent 2); attention and eye movements (normal 0, abnormal 1); posture (normal 0, abnormal trunk+1, abnormal limbs+1, abnormal tail+1, or grossly abnormal 4); balance/co-ordination (normal 0, impaired 1, unstable 2, spontaneous falls 3); vocalisation (normal 0, reduced 1, absent 2); motility (normal 0, bradykinesia/hyperkinesia 1, akinesia/hyperkinesia 2). Sedation was noted if present. Disability 'On-time' was defined as the period of time the animals showed a disability score of 6 or less ('On threshold').

Data and Statistical Analysis: Data are presented as median locomotor activity (counts/30 min) or disability score (score over 10 min/30 min) over the 7 hour period of the experiment, or as total locomotor activity (counts/420 min) or disability (total score over 420 min). Data were analysed by Kruskall Wallis ANOVA and post-hoc Man-Whitney test where appropriate. Analyses were corrected for multiple comparisons using the formula:

Acceptable probability=α/number of comparisons
where α=5%

A separate group of animals from those used in the study were treated with vehicle and were used for statistical comparison.

Example 2

Effects of bifeprunox on L-DOPA Induced Reversal of Motor Disabilities

Figure 3:
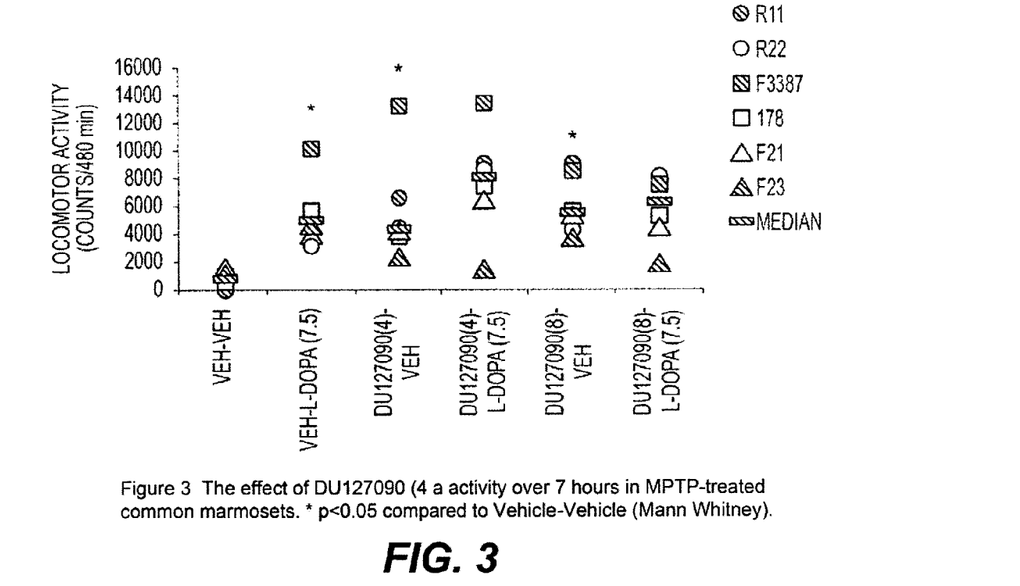
FIG. 3 depicts the effect of bifeprunox (4 a activity) over 7 hours in MPTP treated common marmosets. *p,0.05 compared to Vehicle-Vehicle (Mann Whitney).
Figure 4:
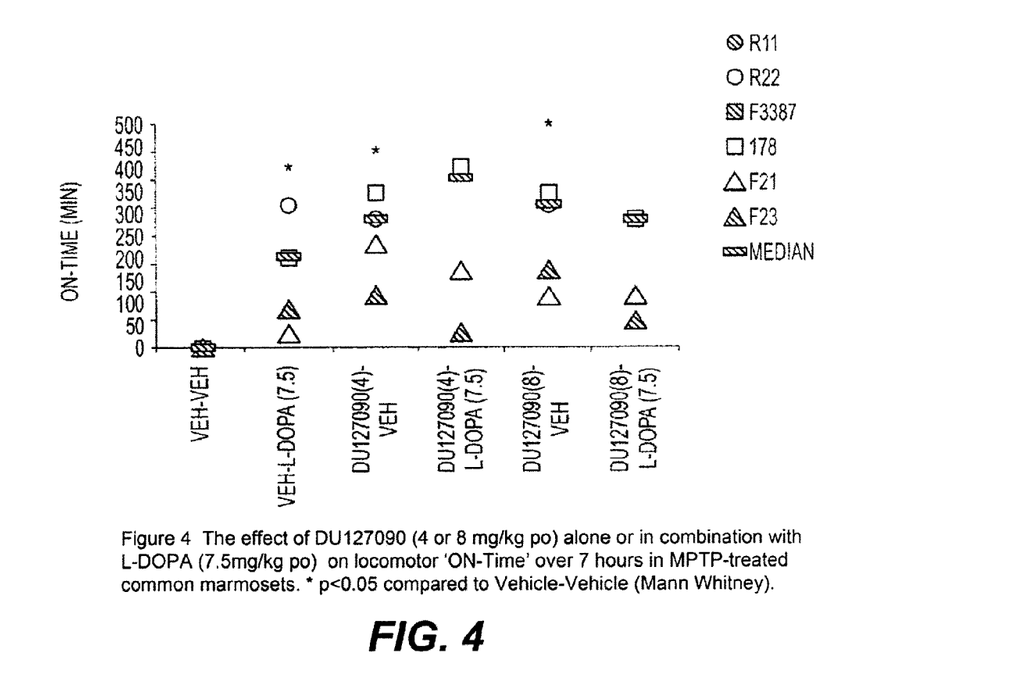
FIG. 4 depicts the effect of bifeprunox (4 or 8 mg/kg p.o.) alone or in combination with L-DOPA (7.5 mg/kg p.o.) on locomotor 'ON-Time' over 7 hours in MPTP treated common marmosets. *p<0.05 compared to Vehicle-Vehicle (Mann Whitney).

Locomotor Activity: L-DOPA (7.5 mg/kg po) plus carbidopa (12.5 mg/kg po 30 min prior to L-DOPA) increased locomotor activity compared to vehicle administration (FIGS. 1, 2, 3 and 4) immediately after administration. Peak activity (median 1627, range 832-2289 counts per 30 min) was reached between 60 and 180 min after administration of L-DOPA. The median duration of activity (On-Time) was 180 min/420 min (FIG. 4). Total locomotor activity and locomotor 'on-time' was greater than vehicle-treated animals (p<0.05, Mann Whitney).

Bifeprunox (4 mg/kg po) increased locomotor activity compared to vehicle administration (FIGS. 1 and 3) immediately after administration. Peak activity (median 685, range 512-1967 counts per 30 min) was reached between 60 and 180 min after administration. The median duration of activity (On-Time) was 240 min/420 min (FIG. 4). Total locomotor activity and locomotor 'On-Time' were greater than in vehicle-treated animals (p<0.05, Mann Whitney).

Bifeprunox (8 mg/kg po) increased locomotor activity compared to vehicle administration (FIGS. 2 and 3) immediately after administration. Peak activity (median 1110, range 669-2058 counts per 30 min) was reached between 60 and 300 min after administration. The median duration of activity (On-Time) was 345 min/420 min was greater than vehicle treatment (FIG. 4). Total locomotor activity was greater than vehicle-treated animals (p<0.05, Mann Whitney).

Pretreatment with bifeprunox (4 mg/kg po), 90 min prior to L-DOPA (7.5 mg/kg po) plus carbidopa (12.5 mg/kg po, 30 min prior to L-DOPA), increased locomotor activity compared to baseline (FIGS. 2 and 3) immediately after administration. Peak activity (median 1581, range 556-2232 counts per 30 min) was reached between 60 to 390 min after administration. The median duration of activity (On-Time, 390 min/420 min, FIG. 4) was slightly greater than that seen after L-DOPA alone and bifeprunox. Locomotor activity tended to increase compared to L-DOPA alone and bifeprunox (4 mg/kg po) alone (FIGS. 1, 2, 3 and 4).

Figure 1:
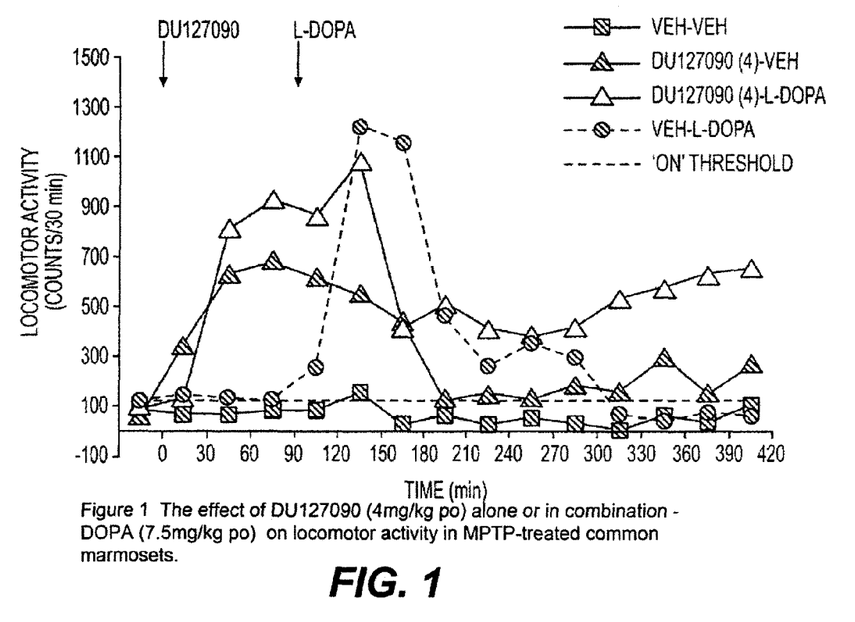
FIG. 1 depicts the effect of bifeprunox (4 mg/kg/p.o.) alone or in combination with L-DOPA (7.5 mg/kg p.o. on locomotor activity in MPTP treated common marmosets).
Figure 2:
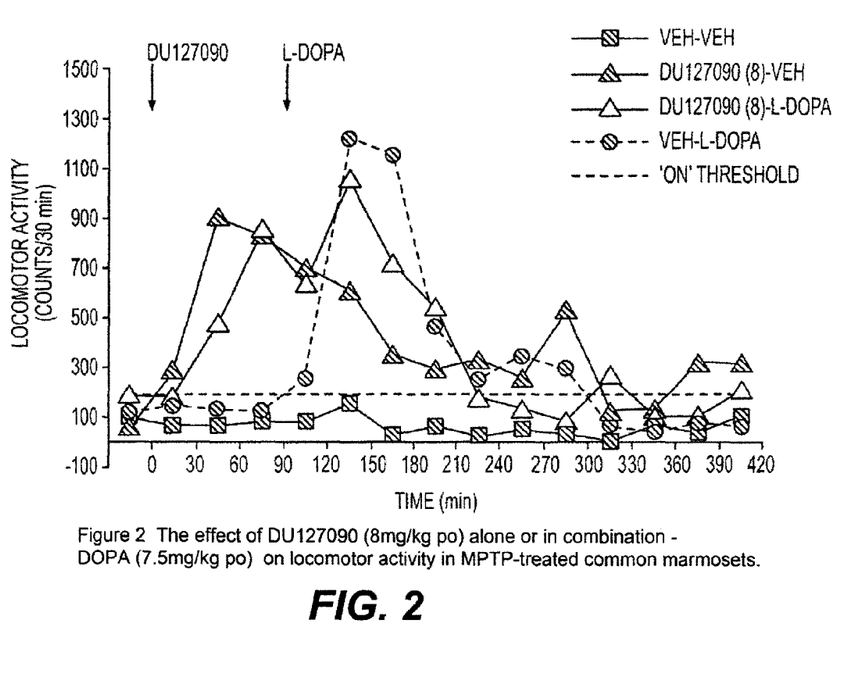
FIG. 2 depicts the effect of bifeprunox (8 mg/kg/p.o.) alone or in combination with L-DOPA (7.5 mg/kg p.o. on locomotor activity in MPTP treated common marmosets).

Pretreatment with bifeprunox (8 mg/kg po), 90 min prior to L-DOPA (7.5 mg/kg po) plus carbidopa (12.5 mg/kg po 30 min prior to L-DOPA), increased locomotor activity compared to baseline (FIGS. 2 and 3) immediately after administration. Peak activity (median 1211, range 409-1342 counts per 30 min) was reached between 60 and 360 min after administration. The median duration of activity (On-Time, 300 min/420 min, FIG. 4) was slightly shorter than bifeprunox alone. Total locomotor activity and duration of activity (On-time) was not different when compared to bifeprunox (8 mg/kg po) alone and L-DOPA (7.5 mg/kg po) plus carbidopa (12.5 mg/kg po 30 min prior to L-DOPA) alone (FIGS. 2, 3 and 4).

Disability: L-DOPA (7.5 mg/kg po) plus carbidopa (12.5 mg/kg po 30 min prior to L-DOPA) decreased disability scores compared to vehicle administration (FIG. 5, 6, 7 and 8) immediately after administration (p<0.05 compared to vehicle treated control, Mann Whitney). Peak activity (median score, 3; score range 2-4) was reached between 30 and 300 (median 75) minutes after administration of L-DOPA. The disability 'On-Time' for L-DOPA alone was 120 min/420 min.

Bifeprunox (4 mg/kg po) decreased disability scores compared to vehicle administration (FIGS. 5 and 7) immediately (30-60 min) after administration (p<0.05 compared to vehicle-treated control, Mann Whitney). Peak scores (median score 3, score range 2-4) were reached between 30 and 240 min after administration. Median duration of activity (On-Time) was 210 min/420 min (FIG. 8).

Bifeprunox (8 mg/kg po) decreased disability scores compared to vehicle treatment immediately after administration (FIGS. 6 and 7) (p<0.05 compared to vehicle treated control, Mann Whitney). Total decrease in disability was lower than vehicle-treated animals (FIG. 7). Peak scores (median 4, range 2-5) were reached between 30 and 150 min after administration. Duration of activity (On-Time) was 225 min/420 min was greater than vehicle treatment (FIG. 8).

Figure 5:
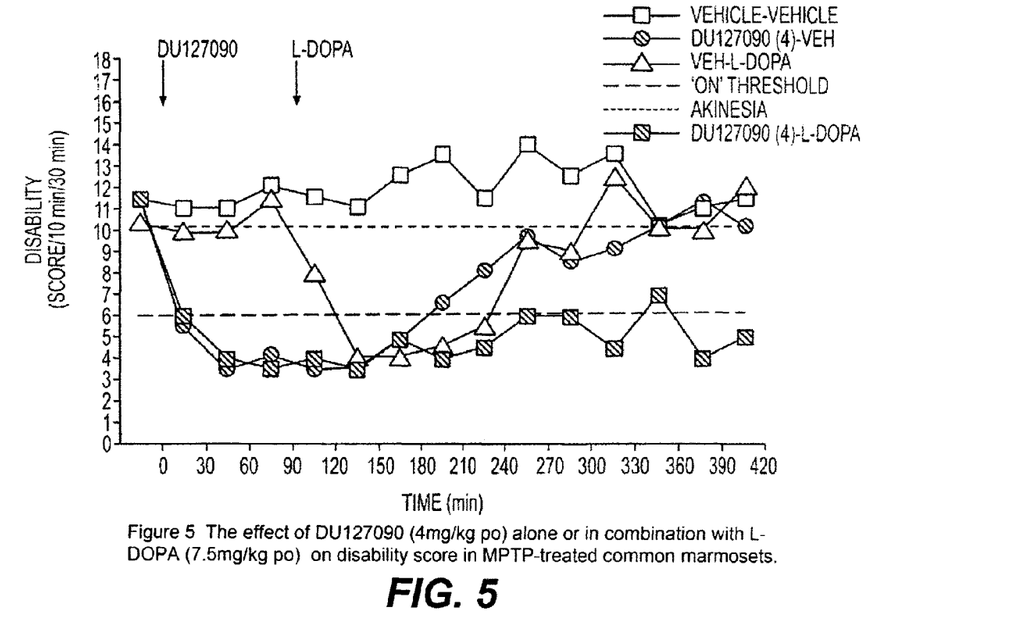
FIG. 5 depicts the effect of bifeprunox (4 mg/kg/p.o.) alone or in combination with L-DOPA (7.5 mg/kg p.o.) on disability score in MPTP treated common marmosets.

Pretreatment with bifeprunox (4 mg/kg po), 90 min prior to L-DOPA (7.5 mg/kg po) plus carbidopa (12.5 mg/kg po 30 min prior to L-DOPA), decreased disability scores over the period of the study. (FIGS. 5 and 7). Peak scores (median 3, range 2-4) were reached between 60 and 240 min after administration. Duration of activity (On-Time) was 360 min/420 min. Duration of activity tended to increase compared to bifeprunox alone (FIG. 8).

Figure 6:
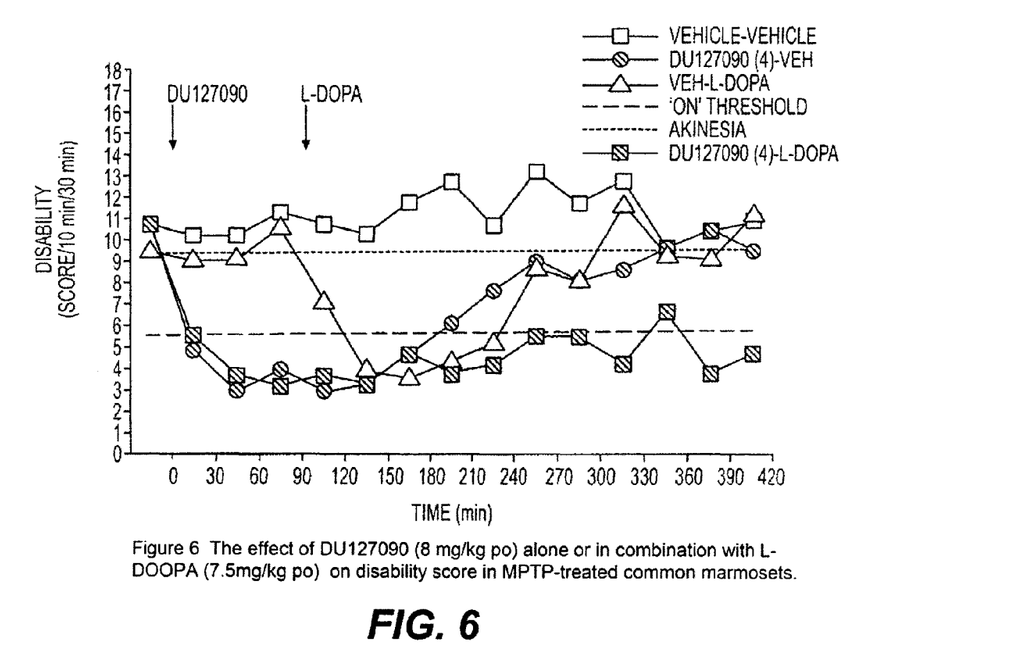
FIG. 6 depicts the effect of bifeprunox (8 mg/kg/p.o.) alone or in combination with L-DOPA (7.5 mg/kg p.o.) on disability score in MPTP treated common marmosets.
Figure 7:
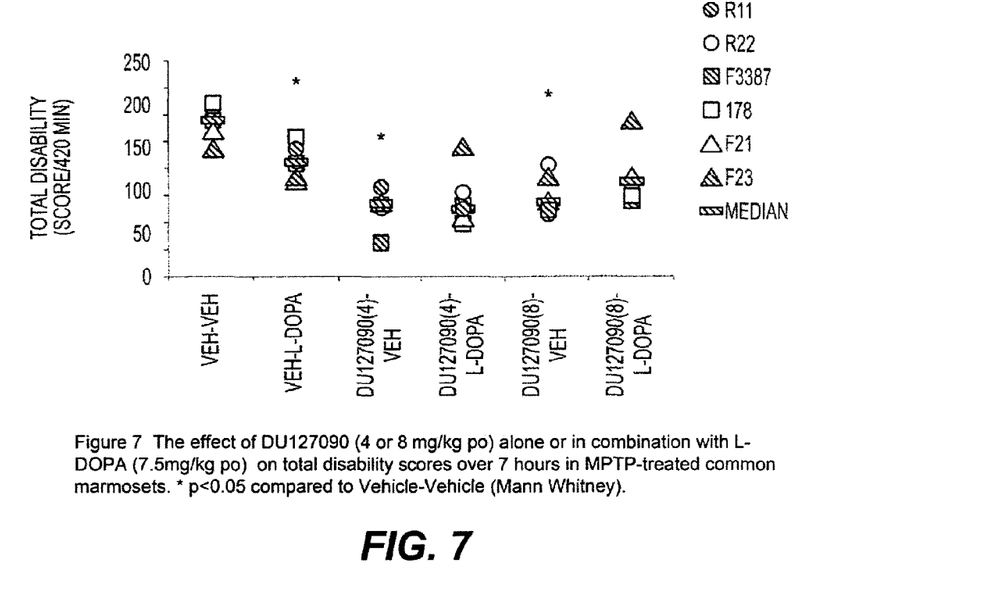
FIG. 7 depicts the effect of bifeprunox (4 or 8 mg/kg/p.o.) alone or in combination with L-DOPA (7.5 mg/kg p.o.) on total disability scores over 7 hours in MPTP treated common marmosets. *p<0.05 compared to Vehicle-Vehicle (Mann Whitney).
Figure 8:
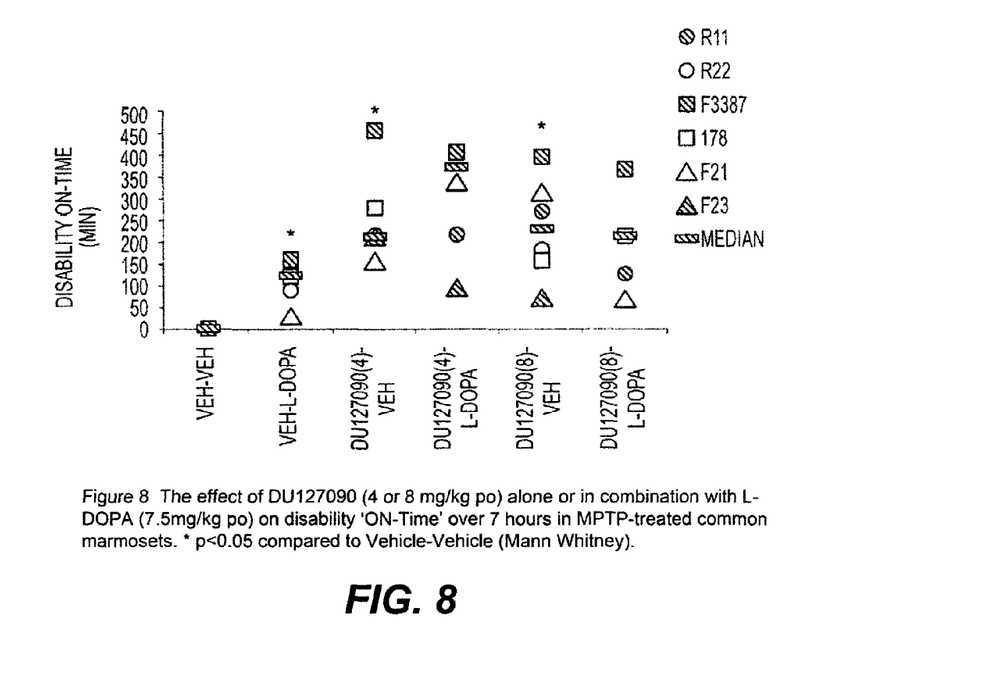
FIG. 8 depicts the effect of bifeprunox (4 or 8 mg/kg/p.o.) alone or in combination with L-DOPA (7.5 mg/kg p.o.) on total disability 'ON-Time' over 7 hours in MPTP treated common marmosets. *p<0.05 compared to Vehicle-Vehicle (Mann Whitney).

Pretreatment with bifeprunox (8 mg/kg po), 90 min prior to L-DOPA (7.5 mg/kg po) plus carbidopa (12.5 mg/kg po 30 min prior to L-DOPA), decreased disability scores, (FIGS. 6 and 7). Peak scores (median 3, range 2-5) were reached between 60 and 120 min after administration. Duration of activity (On-Time) was 165 min/420 min. Duration of activity was not different to either bifeprunox (8 mg/kg po) alone or L-DOPA (7.5 mg/kg po) plus carbidopa (12.5 mg/kg po 30 min prior to L-DOPA) (FIG. 8).

Conclusion: L-DOPA (7.5 mg/kg po) increased locomotor activity and decrease disability scores in MPTP-treated common marmosets. Bifeprunox (4 and 8 mg/kg po) also increased locomotor activity and decreased disability scores. When given in combination with L-DOPA, bifeprunox (4 or 8 mg/kg po) tended to increase total locomotor activity and locomotor 'On-Time' compared to L-DOPA alone.

Example 3

Pharmaceutical Preparations

Types of pharmaceutical compositions that may be used include, but are not limited to, tablets, chewable tablets, capsules (including microcapsules), solutions, parenteral solutions, ointments (creams and gels), suppositories, suspensions, and other types disclosed herein or apparent to a person skilled in the art from the specification and general knowledge in the art. The compositions are used for oral, intravenous, subcutaneous, tracheal, bronchial, intranasal, pulmonary, transdermal, buccal, rectal, parenteral or other ways to administer. The pharmaceutical formulation contains at least one preparation of the invention in admixture with a pharmaceutically acceptable adjuvant, diluent and/or carrier. In some embodiments, the total amount of active ingredients is in the range of from about 0.1% (w/w) to about 95% (w/w) of the formulation, such as from about 0.5% to about 50% (w/w) and further, for example, from about 1% to about 25% (w/w). The molar ratio between bifeprunox (or its N-oxide) and L-DOPA may be in the range of from about 1000:1 to about 1:1000, such as in the range of from about 300:1 to about 1:300, and further, for example, from about 50:1 to about 1:50.

The preparations of the invention can be brought into forms suitable for administration by means of usual processes using auxiliary substances such as liquid or solid, powdered ingredients, such as the pharmaceutically customary liquid or solid fillers and extenders, solvents, emulsifiers, lubricants, flavorings, colorings and/or buffer substances. Frequently used auxiliary substances include magnesium carbonate, titanium dioxide, lactose, saccharose, sorbitol, mannitol and other sugars or sugar alcohols, talc, lactoprotein, gelatin, starch, amylopectin, cellulose and its derivatives, animal and vegetable oils such as fish liver oil, sunflower, groundnut or sesame oil, polyethylene glycol and solvents such as, for example, sterile water and mono- or polyhydric alcohols such as glycerol, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatine capsules may be prepared with capsules containing a mixture of the active ingredients of the invention, vegetable oil, fat, or other suitable vehicle for soft gelatine capsules. Hard gelatine capsules may contain granules of the active ingredients. Hard gelatine capsules may also contain the active ingredients together with solid powdered ingredi- ents such as lactose, saccharose, sorbitol, mannitol, potato starch, corn starch, amylopectin, cellulose derivatives or gelatine. Dosage units for rectal administration may be prepared (i) in the form of suppositories that contain the active substance mixed with a neutral fat base; (ii) in the form of a gelatine rectal capsule that contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups, elixirs, concentrated drops or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder, reconstituted with a suitable solvent prior to use. Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation, reconstituted with a suitable solvent before use.

Also provided according to the present invention are formulations and 'kits of parts' comprising one or more containers filled with one or more of the ingredients of a pharmaceutical composition of the invention, for use in medical therapy. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration. The use of formulations of the present invention in the manufacture of medicaments for use in treating a condition in which recovery of dopaminergic function is required or desired, and methods of medical treatment or comprising the administration of a therapeutically effective total amount of at least one preparation of the invention to a patient suffering from, or susceptible to, a condition in which recovery of dopaminergic function is required or desired.

What is claimed is:

1. A composition comprising (i) from 0.01 mg/kg to 4 mg/kg of bifeprunox or its N-oxide:

Bifeprunox bifeprunox N-oxide or at least one pharmacologically acceptable salt thereof, (ii) L-DOPA, or at least one pharmacologically acceptable salt thereof, and (iii) a decarboxylase inhibitor chosen from carbidopa and benserazide, for simultaneous, separate or sequential use in therapy of at least one disorder requiring recovery of dopaminergic function.

2. A composition as claimed in claim 1, further comprising a catecholamine-O-methyltransferase inhibitor.

3. A composition as claimed in claim 2, wherein the catecholamine-O-methyltransferase inhibitor is chosen from entacapone, nitecapone and tolcapone.

4. A composition as claimed in claim 1, further comprising an monamine oxidase-B inhibitor.

5. A composition as claimed in claim 4, wherein the monamine oxidase-B inhibitor is chosen from deprenyl, (−)-deprenyl, desmethyldeprenyl, N-propargyl-1-(R)-aminoindan, phenelzine, tranyl-cypromine, CGP3466, furazolidone, isocarboxazid, pargyline, methyclothiazide and procarbazine.

6. A method for manufacturing a medicament for treating at least one disorder requiring recovery of dopaminergic function, said method comprising preparing a composition comprising (i) from 0.01 mg/kg to 4 mg/kg of bifeprunox or its N-oxide:

Bifeprunox bifeprunox N-oxide or at least one pharmacologically acceptable salt thereof, (ii) L-DOPA or at least one pharmacologically acceptable salt thereof, and (iii) a decarboxylase inhibitor chosen from carbidopa and benserazide.

7. The method as claimed in claim 6, wherein said at least one disorder is Parkinson's disease.

8. The method as claimed in claim 6, wherein said at least one disorder is restless leg syndrome.

9. A pharmaceutical composition comprising, at least one of a pharmaceutically acceptable carrier and a pharmaceutically acceptable auxiliary substance, and a pharmacologically active amount of a composition comprising (i) from 0.01 mg/kg to 4 mg/kg of bifeprunox or its N-oxide:

or at least one pharmacologically acceptable salt thereof, (ii) L-DOPA or at least one pharmacologically acceptable salt thereof and (iii) a decarboxylase inhibitor chosen from carbidopa and benserazide.

10. A method for treating Parkinson's disease or restless leg syndrome, in a human or animal patient in need of such treating, said method comprising administering to the patient simultaneously, separately or sequentially, from 0.01 mg/kg to 4 mg/kg of bifeprunox or its N-oxide, or at least one pharmacologically acceptable salt thereof, a therapeutically effective amount of L-DOPA or at least one pharmacologically acceptable salt thereof, and a therapeutically effective amount of at least one decarboxylase inhibitor chosen from carbidopa and benserazide.

11. The method as claimed in claim 10, further comprising administering a pharmacologically acceptable amount of at least one of a catecholamine-O-methyltransferase inhibitor and an monamine oxidase-B inhibitor.

12. A kit comprising:
   (i) a vessel containing from 0.01 mg/kg to 4 mg/kg of bifeprunox, its N-oxide, or at least one pharmacologically acceptable salt thereof,
   (ii) a vessel containing L-DOPA or at least one pharmacologically acceptable salt thereof,
   (iii) a vessel containing a decarboxylase inhibitor chosen from carbidopa and benserazide, and
   (iv) instructions for the sequential, separate or simultaneous administration of bifeprunox, L-DOPA, and a decarboxylase inhibitor to a patient in need thereof.

13. A method for preparing a kit comprising bringing a vessel containing (i) from 0.01 mg/kg to 4 mg/kg of bifeprunox, its N-oxide, or at least one pharmacologically acceptable salt thereof into association with (ii) a vessel containing L-DOPA or at least one pharmacologically acceptable salt thereof, and (iii) a vessel containing a decarboxylase inhibitor chosen from carbidopa and benserazide.

* * * * *